US012646625B2

(12) United States Patent
Dcruz et al.

(10) Patent No.: US 12,646,625 B2
(45) Date of Patent: Jun. 2, 2026

(54) SYSTEM, METHOD AND APPARATUS FOR NON-INVASIVE AND NON-CONTACT MONITORING OF HEALTH RACTERSTICS USING ARTIFICIAL INTELLIGENCE (AI)

(71) Applicant: DOCSUN BIOMED LIMITED, Tortola (GB)

(72) Inventors: Julian Gerald Dcruz, Kollam (IN); Pai-Chang Yeh, Zhubei (TW)

( * ) Notice: Subject to any disclaimer, the term of this patent is extended or adjusted under 35 U.S.C. 154(b) by 494 days.

(21) Appl. No.: 17/729,523

(22) Filed: Apr. 26, 2022

(65) Prior Publication Data

US 2022/0254502 A1     Aug. 11, 2022

Related U.S. Application Data

(60) Provisional application No. 63/180,385, filed on Apr. 27, 2021.

(51) Int. Cl.
| | |
|---|---|
| *G16H 50/30* | (2018.01) |
| *G06V 10/82* | (2022.01) |
| *G06V 20/40* | (2022.01) |
| *G06V 40/16* | (2022.01) |
| *G16H 15/00* | (2018.01) |
| *G16H 30/40* | (2018.01) |

(52) U.S. Cl.
CPC ............. *G16H 50/30* (2018.01); *G06V 10/82* (2022.01); *G06V 20/46* (2022.01); *G06V 40/161* (2022.01); *G16H 15/00* (2018.01); *G16H 30/40* (2018.01)

(58) Field of Classification Search
CPC ................................................. G06V 40/171
See application file for complete search history.

(56) References Cited

U.S. PATENT DOCUMENTS

| | | | | |
|---|---|---|---|---|
| 11,051,701 | B1 * | 7/2021 | Gaines | ...................... G06T 7/73 |
| 2013/0023738 | A1 * | 1/2013 | Chang | ...................... A61B 5/01 |
| | | | | 600/301 |
| 2018/0206798 | A1 * | 7/2018 | Murai | ...................... A61B 5/00 |
| 2020/0397306 | A1 * | 12/2020 | Frank | ........................ G01J 5/10 |
| 2021/0389234 | A1 * | 12/2021 | Mandelis | ............. A61B 5/0075 |

FOREIGN PATENT DOCUMENTS

| | | | | |
|---|---|---|---|---|
| CN | 110363226 | A * | 10/2019 | |
| CN | 111310584 | A * | 6/2020 | ............. A61B 5/024 |
| CN | 110866955 | B * | 2/2024 | ............. G06T 5/002 |

* cited by examiner

*Primary Examiner* — Di Xiao
(74) *Attorney, Agent, or Firm* — Eric Hanscom

(57) ABSTRACT

A non-contact and non-invasive apparatus and method for monitoring of health characteristics of a user. The apparatus includes one or more cameras and processor for real-time video of the user and for processing at least each frame from the obtained real-time video. One or more facial regions are from each processed frame to extract one or more regions of interest present therein. The extracted regions of interest are at least one image based physiological monitoring model along with one or more Photo plethysmography imaging (iPPG) and Optical Coherence Tomography (OCT) variations to process one or more extracted regions of interest and obtain at least one result indicative of the health characteristics of the of user based on the real-time video by using Convolutional Neural Network algorithm. The method can be implemented as an AI based software or a platform. A report can be generated for warning for any abnormal range.

17 Claims, 7 Drawing Sheets

Self-Diagnostic AI Tool Pulse Rate Readings

Oximeter Pulse Rate

SYSTEM, METHOD AND APPARATUS FOR NON-INVASIVE AND NON-CONTACT MONITORING OF HEALTH RACTERSTICS USING ARTIFICIAL INTELLIGENCE (AI)

RELATED APPLICATIONS

This application claims the benefit of U.S. provisional patent application 63/180,385, titled "SELF-DIAGNOSTIC ARTIFICIAL INTELLIGENCE TOOL FOR DETECTION OF RESPIRATORY DISEASES AND SYMPTOMS", filed by Julian Gerald Dcruz on Apr. 27, 2021. This provisional patent application is incorporated herein by reference.

FIELD OF INVENTION

The present invention relates generally to an apparatus, method and a device and a non-invasive and non-contact method for monitoring health characteristics or vital signs of a user.

BACKGROUND

The following description includes information that may be useful in understanding the present invention. It is not an admission that any of the information provided herein is prior art or relevant to the presently claimed invention, or that any publication specifically or implicitly referenced is prior art.

Health care costs currently represent a significant portion of the United States Gross National Product and are generally rising faster than any other component of the Consumer Price Index. Moreover, usually because of an inability to pay for medical services, many people are deprived of access to even the most basic medical care and information.

Many people get delayed in obtaining, or are prevented from seeking, medical attention because of cost, time constraints, or inconvenience. If the public had such a universal, unrestricted, and easy access to medical information, many diseases could be prevented. Likewise, the early detection and treatment of numerous diseases could keep many patients from reaching the advanced stages of illness, the treatment of which is a significant part of the financial burden attributed to our nation's health care system. It is clear that the United States along with other countries are facing health-related issues of enormous proportions and that present solutions are not robust.

Previous attempts at tackling the healthcare problem have involved various forms of automation. Some of these attempts have been in the form of a dial-in library of answers to medical questions. Other attempts have targeted providing doctors with computerized aids for use during a patient examination. These methods involve static procedures or algorithms. What is desired is an automated way of providing to a patient medical advice and diagnosis that is quick, efficient and accurate. Such a medical advice system should be modular to allow expansion for new types of medical problems or methods of detection.

Let discuss some of the important health characteristics of a user, their level and importance in the maintaining them in the range for a healthy life.

Pulse Rate is measured as the number of pulsations in an artery per unit time; the normal ranges are between 60 and 80 beats per minute. The Pulse Rate is used to obtain a quick evaluation of the person's health. In the recent years, the Pulse Rate has become a symbol of fitness among fitness experts and wellness experts with the measurement of Pulse Rate from smart bands and smart watches. These help the user to track their fitness continuously throughout the day.

Pulse Rate levels give you information about how well your heart beats and you can maintain a graphical history of the records on your phone, if it is connected to your smart band. This is especially useful for hypertension and diabetic patients who need to constantly monitor their vitals.

The devices used by health care professionals to monitor Pulse Rate levels include standard pulse-oximeter devices, ECG devices, etc. Pulse Rate is an important vital that provides information about the rate of blood flow through the body, an abnormal Pulse Rate is an important sign that something wrong might be happening (taking into the context of symptoms, other vital signs, trends, etc.)

Another important health characteristics or vital sign is saturated blood oxygen levels (Spo2), which refers to the percentage of oxygen in the blood. The Saturated blood oxygen levels (Spo2) is used to obtain a quick evaluation of the person's health. In the recent years, the saturated blood oxygen levels (Spo2) has become a symbol of fitness among fitness experts and wellness experts with the measurement of saturated blood oxygen levels (Spo2) from smart bands and smart watches. These help the user to track their fitness continuously throughout the day.

The Saturated blood oxygen levels (Spo2) levels give you information about how well your heart beats, how well your oxygen intake and lets you know in advance on how to monitor and tackle fatigue, and you can maintain a graphical history of the records on your phone, if it is connected to your smart band. This is especially useful for hypertension and diabetic patients who need to constantly monitor their vitals.

The devices used by health care professionals to monitor saturated blood oxygen levels (Spo2) levels include standard pulse-oximeter devices. Saturated blood oxygen levels (Spo2) is an important vital that provides information about the rate of blood flow through the body and a measurement of oxygen levels in the blood, an abnormal Saturated blood oxygen levels (Spo2) is an important sign that something wrong might be happening (taking into the context of symptoms, other vital signs, trends, etc.)

Another important health characteristics or vital sign is Blood pressure, which refers to the force exerted by circulating blood on the walls of the arteries, it is measured using two readings: Systolic Readings, which is measured when the heart beats, also referred as when the blood pressure is the highest, and the Diastolic Readings, which is measured between heart beats, when the blood pressure is the lowest. Blood pressure readings are written with the systolic blood pressure first followed by the diastolic blood pressure—as defined by National Cancer Institute.

The Normal range for Blood pressure is less than 120/80 mmHg. Abnormal blood pressure is defined as when the readings don't satisfy the Normal range, the cause of the abnormality maybe due to inherent problems of the user or can be due to stressful environments.

High blood pressure, also called hypertension, is blood pressure that is higher than normal. Your blood pressure changes throughout the day based on your activities. Having blood pressure measures consistently above normal may result in a diagnosis of high blood pressure (or hypertension).

The devices used by health care professionals to monitor blood pressure include Digital Blood pressure Monitor and Sphygmomanometer. These devices involve patient contact with the device which can be categorised as invasive or in-contact.

Monitoring Blood pressure levels continuously can help health care professionals and users to take precaution in their health accordingly; this is especially applicable for patients having cardio-vascular problems. Thus, there is a need for users to have easy access to monitor blood pressure levels with ease and easy accessibility.

Another important health characteristics or vital sign is Respiratory rate, which refers to the rate which breathing occurs or to put it simply, the number of breaths a user takes in a minute (bpm). The Respiratory rate is used to obtain a quick evaluation of the person's health. In the recent years, the Respiratory rate has become a symbol of fitness among fitness experts and wellness experts with the measurement of Respiratory rate from smart bands and smart watches. These help the user to track their fitness continuously throughout the day.

Respiratory rate levels give you information about how well your breathing rate, how well your oxygen intake, and gives a sense of understanding on the normality in your breathing (lung function), and lets you know in advance on how to monitor and tackle fatigue, and you can maintain a graphical history of the records on your phone, if it is connected to your smart band. This is especially useful for hypertension and diabetic patients who need to constantly monitor their vitals.

The devices used by health care professionals to monitor Respiratory rate levels include standard pulse-oximeter devices and Spirometer devices. Respiratory rate is an important vital that provides information about the rate of blood flow through the body, a measurement of oxygen levels in the blood, and a measurement of lung functioning, an abnormal Respiratory rate is an important sign that something wrong might be happening (taking into the context of symptoms, other vital signs, trends, etc.).

Similarly the apparatus and the method configured to measure temperature and/or other health characteristics or vital signs of a user.

An example of a virus COVID-19 is caused by the SARS-CoV-2 virus. The virus, which can cause mild to severe respiratory illness, has now spread globally, including to the United States. The current information available to characterize the spectrum of a clinical illness associated with COVID-19 suggests that symptoms include cough, shortness of breath or difficulty breathing, fever, chills, muscle pain, headache, sore throat, or new loss of taste or smell.

However, the need for such a non-contact and non-invasive apparatus and method is felt in the time of COVID-19, where it is not possible for the user to go outside and checked yourself by a doctor where doctors are not available

SUMMARY

The invention presented here provides an apparatus and a method for the non-invasive monitoring of health characteristics such as but not limited to Pulse Rate, Saturated blood oxygen levels (Spo2), blood pressure, respiratory rate and related diseases.

The solution is developed across multiple platforms for the ease of access and use for users. The solution consists of the DOCSUN Health Monitoring Web and Mobile Application, also another solution involves DOCSUN DC Series Doorway Terminal Devices (For the Purpose of Public places) and other solutions including but not limited to planting in chips for multiple AI products.

A non-contact and non-invasive apparatus and a method for monitoring of health characteristics of a user, the non-invasive method comprising: obtaining, by one or more cameras, a real-time video of the user; processing, by a processor, at least each frame from the obtained real-time video; and extracting, by the processor, one or more facial regions from the each of the processed frames to thereby extract one or more regions of interest present therein; feeding, by the processor, the one or more extracted regions of interest to at least one image based physiological monitoring model along with one or more Photo plethysmography imaging (iPPG) and Optical Coherence Tomography (OCT) variations to process the one or more extracted regions of interest and obtain at least one result indicative of the pulse rate level of the of user based on the real-time video by using Convolutional Neural Network algorithm and transmitted to AI data base by using the software and going through the platform, and a non-invasive and non-contact report will be quickly and correctively produced for health characteristics such as pulse rate or respiration rate or blood oxygen levels (Spo2) or blood pressure or temperature of the user which may provide warning for any abnormal range.

The present invention relates to apparatus, method and a device for non-contact & non-invasive monitoring of pulse rate, Spo2, blood pressure, respiratory rate caused due to variations in pulse rate, blood oxygen, temperature and blood pressure. The apparatus includes a camera to obtain a real-time video of the user. Such real-time video can be forwarded to a processor and an AI database via a platform. The processor is configured to process at least each frame from the obtained real-time video to obtain at least one result indicative of the pulse rate level, blood oxygen and blood pressure level of the user.

The Self Diagnostic AI tool is intended to be used for the prediction of the physiological state and health characteristics such as but not limited to Pulse Rate, Saturated blood oxygen levels (Spo2), blood pressure, respiratory rate and related diseases of the user. A Diagnosis Summary is generated based on the prediction of the Physiological state and health characteristics such as but not limited to Pulse Rate, Saturated blood oxygen levels (Spo2), blood pressure, respiratory rate and related diseases of the user, the summary contains information of symptoms of infection or normal state.

The DOCSUN Health Monitoring system provides a method and solution for Users to have a safe and easy understanding of their health and wellness by having a scan of their vitals in the DOCSUN Device Terminals or Web/App interfaces. The DOC SUN Device terminals function in a continuous fashion to help screen and monitor user health and wellness, this has multiple use-cases in offices calling back employees but want to make sure that their employees have a safe and easy understanding of their health. The DOC SUN Device Terminals can help bring a safe and easy understanding to multiple industries, saving and preserving human life by monitoring your health and wellness.

The requirements for the software to analyze and give proper monitoring of Pulse Rate, Saturated blood oxygen levels (Spo2), blood pressure and respiratory rate is that the device running the software requires good high-quality camera and the user should be seen in well-lit environment with sufficient light on the face. The user should refrain from using any type of eye-lens, make-up and mask objects that cover his/her facial regions.

The invention provides a simple and Easy to access interface for user to measure Pulse Rate, Saturated blood oxygen levels (Spo2), blood pressure, and respiratory rate in a non-invasive and non-contact method from his phone or in a public place. DOCSUN Health Monitor can be setup to monitor Pulse Rate levels continuously for users. Cost-effective solution compared to medical devices. The invention utilizes State of the Art Technology AI to power the device.

The AI system processes the video in real-time, it denoises the video frames and extracts both the raw iPPG information and the filtered iPPG information to run through the layers for the prediction of the selected physiological parameters. The generated prediction is then run through a word embedding to generate the diagnosis for the prediction. The results are loaded on the display in less than 10 seconds. The user is thus able to use this information for self-diagnosis or consult with a medical professional.

DETAILED DESCRIPTION OF DRAWINGS

The present invention relates to apparatus, method and a device for non-contact & non-invasive pulse rate monitoring, Saturated blood oxygen levels (Spo2), Blood pressure, respiratory rate and related diseases caused due to variations in pulse rate, blood oxygen level, blood pressure and respiration respectively. The apparatus includes a camera to obtain a real-time video of the user. Such real-time video can be forwarded to a processor and an AI database via a platform. The processor is configured to process at least each frame from the obtained real-time video to obtain at least one result indicative of the pulse rate level of the of user and provide warning related to diseases caused due to variations in pulse rate, blood oxygen, blood pressure and respiratory rate.

The Invention is developed in C–Language, C++Language, java-script and python utilizing capabilities for multiple platform developments on web, android, ios, windowsX86 and linuxX86 based devices. The software requires the use of an optical camera.

A non-contact and non-invasive system, apparatus and method for monitoring of health characteristics of a user, the non-invasive method comprising: obtaining, by one or more cameras, a real-time video of the user; processing, by a processor, at least each frame from the obtained real-time video; and extracting, by the processor, one or more facial regions from the each of the processed frames to thereby extract one or more regions of interest present therein; feeding, by the processor, the one or more extracted regions of interest to at least one image based physiological monitoring model along with one or more Photo plethysmography imaging (iPPG) and Optical Coherence Tomography (OCT) variations to process the one or more extracted regions of interest and obtain at least one result indicative of the pulse rate level of the of user based on the real-time video by using Convolutional Neural Network algorithm and transmitted to AI data base by using the software and going through the platform, and a non-invasive and non-contact report will be quickly and correctively produced for health characteristics such as pulse rate or respiration rate or blood oxygen levels (Spo2) or blood pressure or temperature of the user which may provide warning for any abnormal range.

Figure 1A:
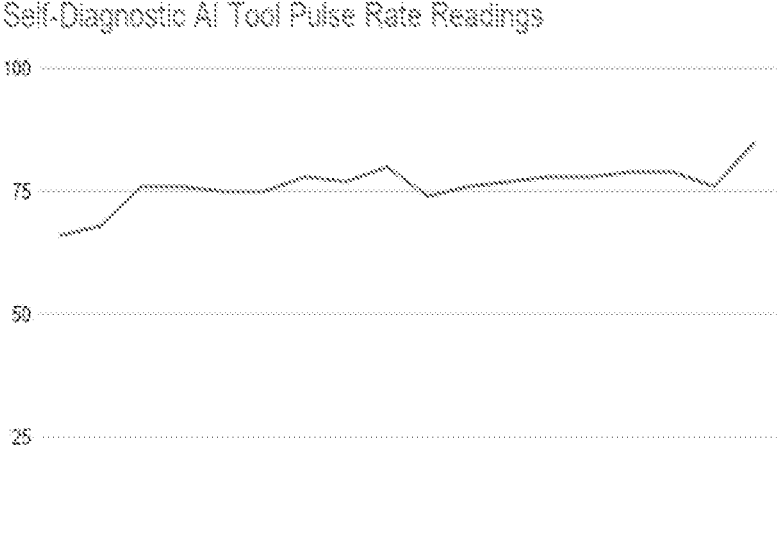
FIGS. 1A-1B illustrates the graphical plot depicting Pulse Rate Readings from Self-Diagnostic AI tool and Oximeter Pulse meter, in an embodiment of the present invention.
Figure 1B:
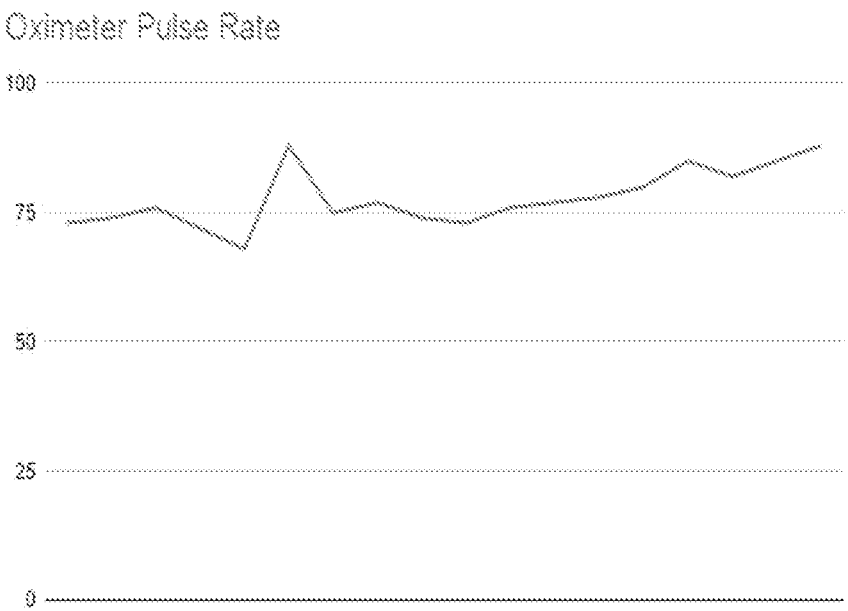

FIGS. 1A-1B illustrates the graphical plot depicting Pulse Rate Readings from Self-Diagnostic AI tool and Oximeter Pulse meter, in an embodiment of the present invention. The graphical illustration helps in understanding the accuracy and error rate with the use of non-contact and non-invasive apparatus and method.

Figures 2A, 2B:
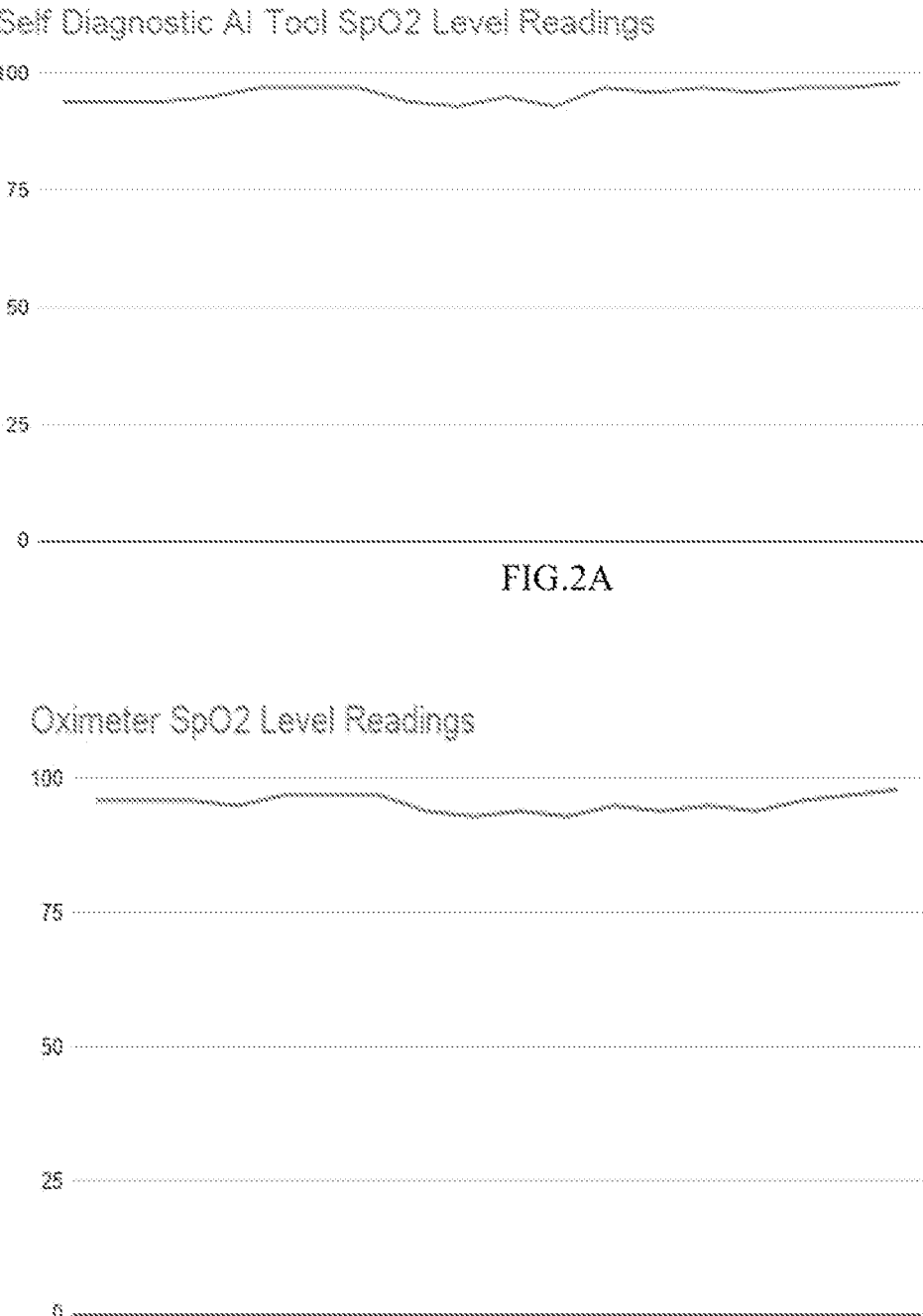
FIGS. 2A-2B illustrates the graphical plot depicting SpO2 reading from Self-Diagnostic AI tool and Oximeter spo2 level readings, in an embodiment of the present invention.

FIGS. 2A-2B illustrates the graphical plot depicting SpO2 reading from Self-Diagnostic AI tool and Oximeter spo2 level readings, in an embodiment of the present invention. The graphical illustration helps in understanding the accuracy and error rate with the use of non-contact and non-invasive apparatus and method.

Figure 3A:
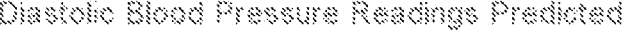
FIGS. 3A-3B illustrates the graphical plot depicting Diastolic Blood pressure reading predicted and Diastolic Blood pressure reading recorded, in an embodiment of the present invention.
Figure 3A:
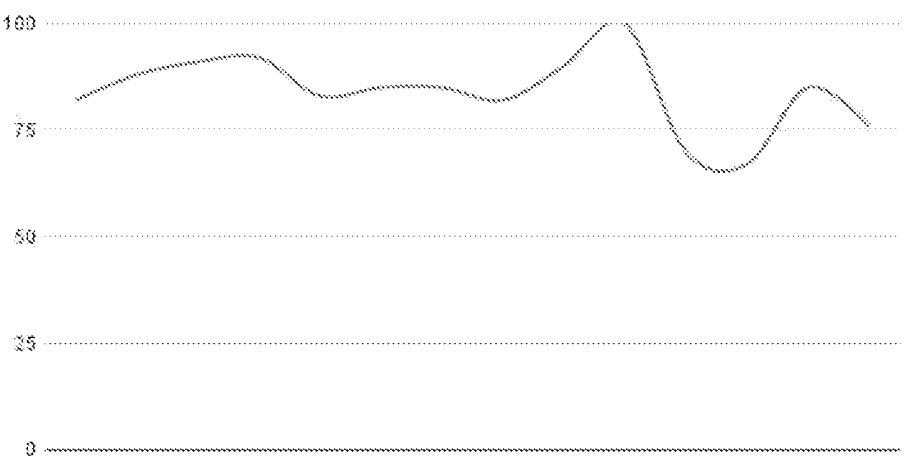
Figure 3B:

FIGS. 3A-3B illustrates the graphical plot depicting Diastolic Blood pressure reading predicted and Diastolic Blood pressure reading recorded, in an embodiment of the present invention. The graphical illustration helps in understanding the accuracy and error rate with the use of non-contact and non-invasive apparatus and method.

Figure 4A:
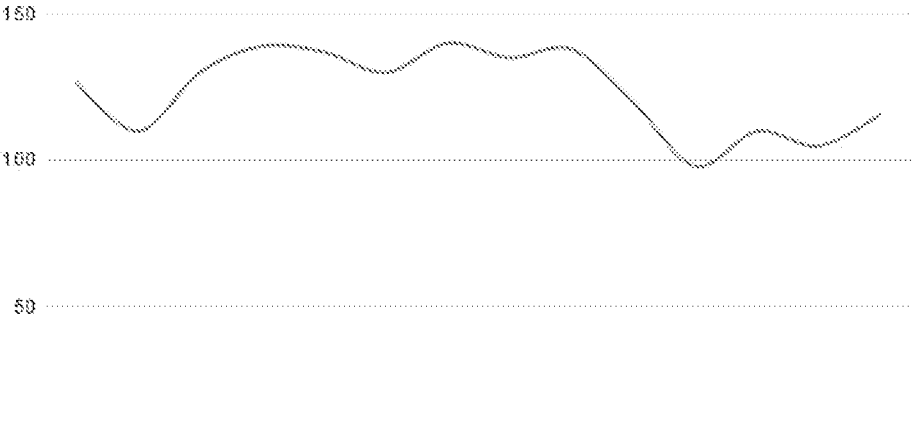
FIGS. 4A-4B illustrates the graphical plot depicting systolic Blood pressure reading predicted and systolic Blood pressure reading predicted, in an embodiment of the present invention.
Figure 4B:
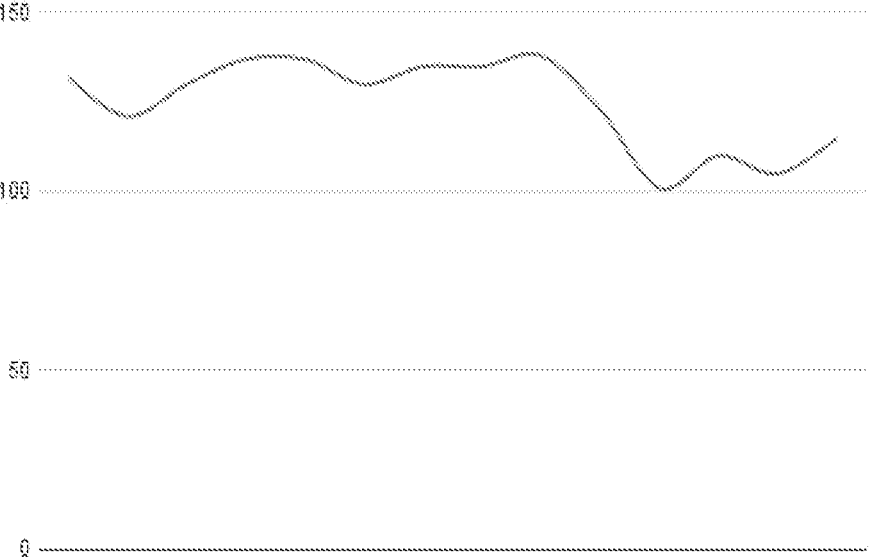

FIGS. 4A-4B illustrates the graphical plot depicting systolic Blood pressure reading predicted and systolic Blood pressure reading predicted, in an embodiment of the present invention. The graphical illustration helps in understanding the accuracy and error rate with the use of non-contact and non-invasive apparatus and method.

Figures 5A, 5B:
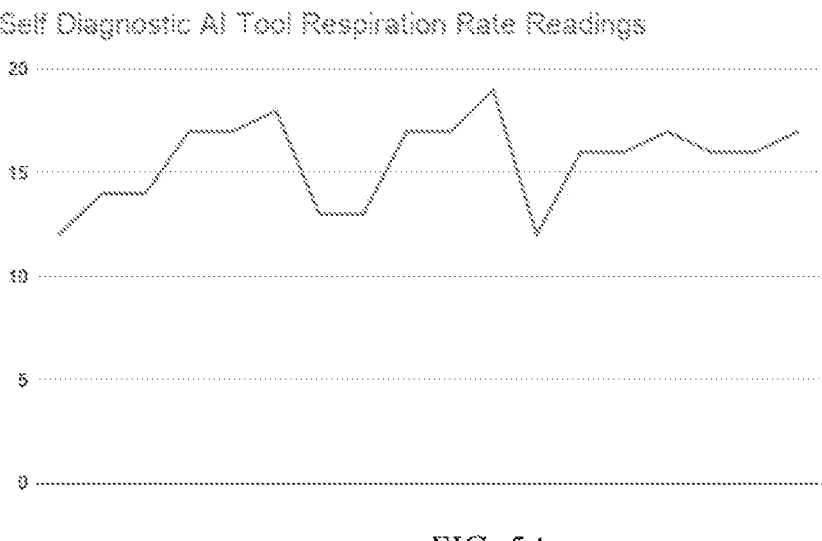
FIGS. 5A-5B illustrates the graphical plot depicting respiration Rate Readings from Self-Diagnostic AI tool and respiration rate through manual observation, in an embodiment of the present invention.

FIGS. 5A-5B illustrates the graphical plot depicting respiration Rate Readings from Self-Diagnostic AI tool and respiration rate through manual observation, in an embodiment of the present invention. The graphical illustration helps in understanding the accuracy and error rate with the use of non-contact and non-invasive apparatus and method.

Figure 6:
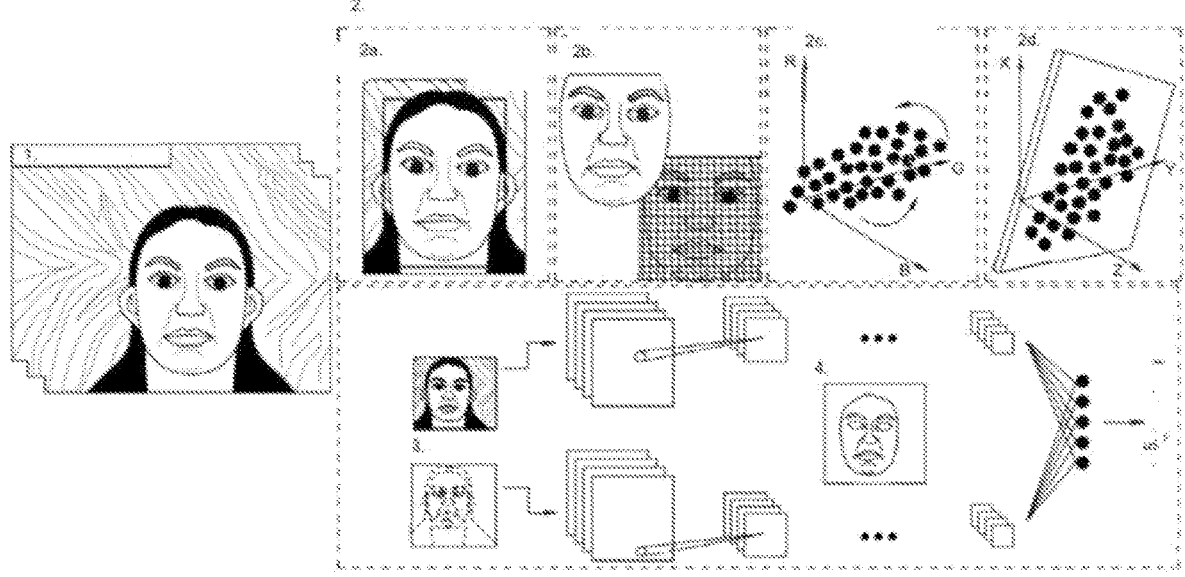
FIG. 6 is the Model processes the facial regions and extracts multi correlating regions of images of users

FIG. 6 is the Model processes the facial regions and extracts multi correlating regions of images of users.

Figure 7:
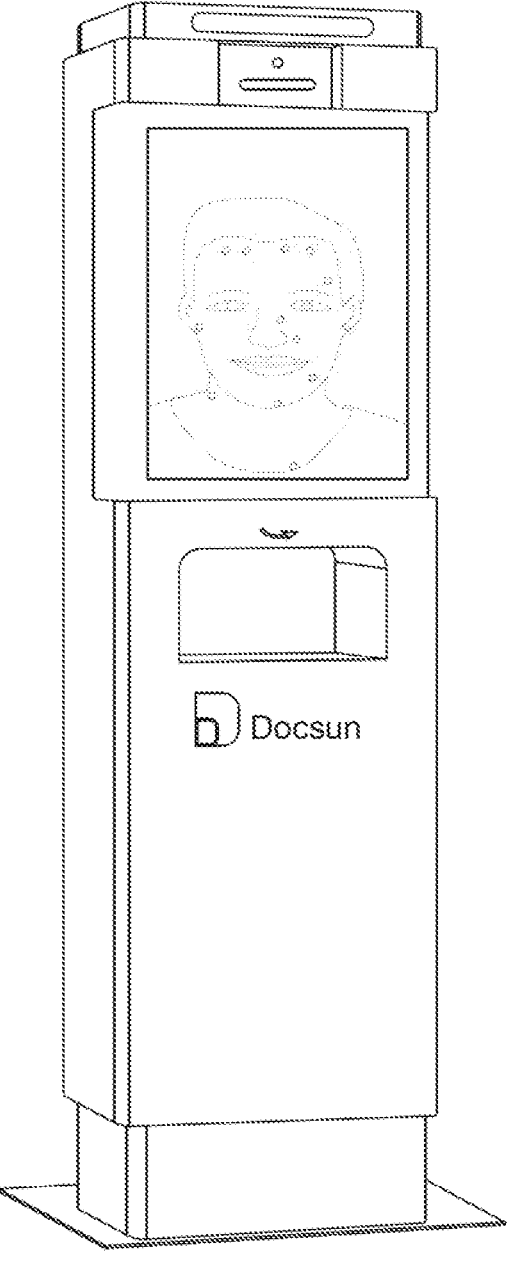
FIG. 7 is the apparatus which processes the facial regions and extracts multi correlating regions of images of users.

FIG. 7 is the apparatus which processes the facial regions and extracts multi correlating regions of images of users. The apparatus comprises a processor, one or more sensors including but not limited to a pulse sensor, respiration sensor, a temperature sensor, blood pressure sensor and Saturated blood oxygen sensor and one or more Photo plethysmography imaging (iPPG) and Optical Coherence Tomography (OCT) to process the collected data from the processor.

A display screen to display at least one result indicative of the health characteristics of the user based on the real-time video by using Convolutional Neural Network algorithm.

A QR or machine code generator to generate the displayed said results related to the health characteristics of the user.

The Software processes real-time video, each frame of the video is processed with de-noising profiles after which we run few layers of varying augmentation profiles. The Facial regions are extracted, and the regions of interest are extracted and filtered before providing it as input to the model. We also supply the iPPG variations into the model as input to add as Correlation labels. These serve to help better the results and add a sense of fine tuning to the readings. The result is then categorized as 3 different alerts—Green Alert (For Healthy), Yellow Alert (Caution) and Red Alert (Abnormal). These alerts provide a sense of understanding and ease to use interface to the user.

The result shown to user consists of Pulse Rate level readings in beats per minute (B.P.M) and also health alert with textual wordings to help user understand the alert.

The result shown to user consists of SPO2 readings in (%) and also health alert with textual wordings to help user understand the alert.

The result shown to user consists of blood pressure level readings in mmHg and also health alert with textual wordings to help user understand the alert.

The result shown to user consists of Respiratory rate level readings in breaths per minute (bpm) and health alert with textual wordings to help user understand the alert.

The alert wordings are: Normal Pulse Rate and Abnormal Pulse Rate Level. The numerical readings are represented in beats per minute (B.P.M).

The alert wordings are: Normal Saturated blood oxygen levels (Spo2) and Abnormal Saturated blood oxygen levels (Spo2). The numerical readings are represented percentage levels (%).

The alert wordings are: Normal Blood Pressure Level, Elevated Blood Pressure Level and Abnormal Blood Pressure Level. The numerical readings are represented as mmHg readings with both systolic and diastolic levels displayed, with the Systolic levels first and followed by the diastolic levels.

The alert wordings are: Normal Respiratory rate Level, and Abnormal Respiratory rate Level. The numerical readings are represented breaths per minute (bpm).

The readings are generated within 15 seconds and provide time-efficient readings and can also be used in a continuous readings state for continuous monitoring in a continuous non-invasive and non-contact way.

A benchmark study was conducted in Kenya and a Laboratory study was conducted in Taiwan to validate the bias, and accuracy for the Pulse Rate, Saturated blood oxygen levels (Spo2) and blood pressure and respiratory rate predictions. The study results showed no substantial variations in bias for populations of different racial origin and skin color. The study was conducted, and a reading from the digital pulse-oximeter and the DOCSUN health monitoring software was compared to calculate the accuracy and the bias.

The Bias for the readings of pulse rate is: less than 2 bpm (beats per minute).

The Bias for the readings of is: less than 2% in case of saturated blood oxygen level (Spo2) level.

The Bias for the readings for blood sugar is: less than 10 mmHg for Systolic Blood Pressure, and less than 5 mmHg for Diastolic Blood pressure.

The Bias for the readings of respiratory rate is: less than 2 bpm.

The Bias was calculated after considering the bias for the device used to validate the accuracy. The Device gave accurate predictions of Pulse Rate, Saturated blood oxygen levels (Spo2) and blood pressure with slight variations; this was identified as artifact noise due to motion and light. The inclusion for factoring into noise from motion and light artifacts are provided as calibration to help maintain the bias and improve readings accuracy. The model performed with 98% accuracy with 2% error rate, the FIGS. 1A-1B graphical plot depicting the study readings for users of different racial origin and skin color.

The non-contact and non-invasive monitoring of pulse rate, saturated blood oxygen levels (Spo2) and blood pressure level of a user, in accordance with an exemplary embodiment of the present disclosure. The Model processes the facial regions and extracts multi correlating regions and we have added an additional filter profile to help bring correlation to the extracted regions before being sent to the model, this brings consistency in predictions and helps improve accuracy.

The invention uses physiological monitoring model along with one or more Photo plethysmography imaging (iPPG) and Optical Coherence Tomography (OCT) variations and an artificial intelligence (AI) or deep learning techniques or comprise of a Convolutional Neural Network (CNN) algorithm or a software to process the one or more extracted regions of interest and obtain at least one result indicative of the pulse rate, blood oxygen and blood pressure level of the of user based on the real-time video.

The software has been designed over an AI model that takes in the end-to-end video as input. The video is denoised and the RGB channels are processed for the prediction of the physiological state after which it is compared with the fine-tuned bracket to give the diagnosis of the patient under observation in the video. The textual representations in diagnosis reports have helped formulate the predicted diagnosis displayed in our software.

The analytical specificity and the performance have been measured by the evaluation of the base hypothesis and the evaluation of the physiological state. For the evaluation of the base of the hypothesis, we use the AI system we have developed for classifying the diseases based on the lung x-ray images that we have received from the hospital for our research.

| True Positives: 5840 | False Positives: 0 |
|---|---|
| False Negatives: 160 | True Negatives: 2000 |

| Total Number of Samples for Validation | Number of Infected from the Sample | Number of Normal cases from the Sample |
|---|---|---|
| 8000 | 6000 | 2000 |

The validation samples are run through the AI system and found that it accurately identified 98% of the cases with the correct labels. We calculated the confusion metrics to estimate the specificity and found the 2% false predictions fell under the condition of false negatives for most of the samples, i.e., the AI system classified the 2% false cases as Normal cases, giving the false classification. These cases were observed to be inclusive of the cases of Lung infection caused due to Infiltration which affected the prediction. As a result, the specificity of the classification was observed to be above 95% in accurately identifying the infected and normal cases from a sample of unknowns. This concluded the evaluation of the base hypothesis study to find the relationship between the lung infected respiratory diseases and the physiological state of the body for early or pre-detection of the disease through the estimation of the physiological parameters estimated by the self-diagnostic software for respiratory diseases such as but not limited to Covid19.

The results from the study on the infection and normal cases identify the use of the physiological state of the body to determine the early or pre-stage detection of the infection using the core vital signs. We evaluated the accuracy of the vital sign's readings provided by the self-diagnostic AI based software by doing a comparative study with the oximeter (BPL PulseOxyO2) device. We studied the accuracy of the readings predicted by the software with the readings recorded with the pulse oximeter device to validate the prediction of the physiological state of the human body.

Error in Pulse Rate: The error percent was computed as a 0.5% Error difference with the pulse oximeter device taking into the environmental variations during observations. The Pulse readings were found to fluctuate drastically when the user moved away from the camera. Readings recorded under ambient lighting with the user observed under minimal motion and with the user's face in proximity with the camera showed good correspondence with the readings recorded with the pulse oximeter device.

Error in Pulse Rate: The error percent was computed as a 0.5% Error difference with the pulse oximeter device taking into the environmental variations during observations. The Pulse readings were found to fluctuate drastically when the user moved away from the camera. Readings recorded under ambient lighting with the user observed under minimal motion and with the user's face in proximity with the camera showed good correspondence with the readings recorded with the pulse oximeter device.

Error in Breathing Rate: The breathing rate was recorded manually for comparison during the time of observation under the software. The Software gave the accurate prediction of the breathing rate of the user with all the test controls satisfied. There was minimum or no variation in the prediction of the breathing rate when compared with the manual observation results.

Error in SpO2 Level: The SpO2 Level comparison was recorded and observed with the pulse oximeter device. The observations were recorded with the self-diagnostic AI based software after the test controls were all satisfied. The error percentage found during the comparison study showed a 1% variation due to environmental changes, but under all the test controls satisfied condition the software showed no comparable difference with the readings recorded on both the oximeter device and the software.

Error in Eye Coloration: There was no significant error for the samples under consideration for eye coloration when all the test controls were satisfied.

The general instructions as mentioned in the previous section is followed, more elaboration on the instructions to follow for usage is mentioned below while using the self-diagnostic AI apparatus are:

Remove any accessories, including glasses and/or mask from the facial area. Stand in front of the device making sure all the facial features are visible on the screen. The User will see the screen shown below, where he/she sees the illustrations of the instructions to follow for a good accurate detection of health status.

The user needs to look straight into the camera. Avoid sudden movements and rapid blinking during the detection. Perform a normal breathing cycle while detection. The user will see the active screen where his live stream is displayed, and he/she sees a detection feedback icon to notify him that the detection is running. This will make the user experience responsive and better.

After the detection is done (approximately 15 seconds), the user sees the results on the screen. The results displayed as summary of his/her diagnosis and if the user is healthy, he/she sees a green "GO" icon otherwise he/she will see a red "Stop" icon.

Also, in another embodiment, the user can send the summary report to his/her or any of his contact via voice command. There need to be a microphone and a speaker attached to the device which communicates with the user. The voice interaction system may be normal or may be done using smart speaker or IOT based speaker system. The smart voice command system may be used to send instructions to the device and the device also communicates with user, if the device is unable to process the voice command properly.

The voice interaction avoid touching the machine for input or output. A QR code or a unique identifier may relate to user. So, with this user, user can check the status of the results from the website or mobile application using QR code and/or the identifier.

In another embodiment, the medical professional may get access to the user results or summary of diagnosis when user shares his/her QR code or identifier with the medical professional. Otherwise the results are private and only known to user.

If the recording of the video is successful the user will receive a notification with the diagnosis, otherwise, he/she will receive an error message and will have to repeat the whole procedure.

When successful a diagnosis summary is generated based on the prediction of the physiological state of the user, the summary contains information of vital signs such as temperature, heart rate, spo2 level, breathing rate, and eye coloration. Depending on this information, the user will receive as shown in the following image the diagnosis "Patient shows no symptoms of infection by respiratory diseases" otherwise; he/she will receive the following message "Patient shows symptoms of infection by respiratory diseases".

The method can be implemented as a doorway system as terminal, desktop software, algorithm, application for mobile or computer and/or a webpage or website.

Advantages

The known and potential benefit of the Self Diagnostic AI Software for clinical use of screening and diagnosis of covid19 are:

Fast and accurate readings of Vital Signs, which are then processed to identify the User's symptoms and detect if the person is infected with Covid19 or healthy.

Quality Assured user experience of the application.

Protection of user privacy

| | |
|---|---|
| Positive Results | Diagnosis shows: "Patient is Unhealthy and shows symptoms of infection for respiratory disease". This prediction is generated by the system when the test controls are valid and the user's physiological vitals under observation/recording fall into the abnormal category. |
| Negative Results | Diagnosis shows: "Patient is healthy and shows no symptoms of infection for respiratory disease". This prediction is generated by the system when the test controls are valid and the user's physiological vitals under observation/recording fall into the normal category. |
| Invalid Results | Diagnosis is invalid: The patient is requested to upload a new recording/observation. |

The known and potential benefit of the Self Diagnostic AI Software for clinical use of screening and diagnosis of covid19 are:

Fast and accurate readings of Pulse Rate, Saturated blood oxygen levels (Spo2) and blood pressure levels, which are then processed to identify the User's symptoms and detect if the person is suffering from hypertension or healthy.

Quality Assured user experience of the application.

No saving of image. Protection of user privacy

The self-diagnostic AI tool is manufactured in compliance with ISO62304 medical devices. Software validation takes place within the environment of an established software life cycle. The software life cycle contains software engineering tasks and documentation necessary to support the software validation effort. In addition, the software life cycle contains specific verification and validation tasks that are appropriate for the intended use of the software such as:

Quality planning

System requirements definition

Detailed software requirements specification

Software design specification

Construction or Coding

Testing

Installation

Operation and Support

Maintenance

As used herein, the term engine refers to software, firmware, hardware, or other component that can be used to effectuate a purpose. The engine will typically include software instructions that are stored in non-volatile memory (also referred to as secondary memory). When the software instructions are executed, at least a subset of the software instructions can be loaded into memory (also referred to as primary memory) by a processor. The processor then executes the software instructions in memory. The processor may be a shared processor, a dedicated processor, or a combination of shared or dedicated processors. A typical program will include calls to hardware components (such as I/O devices), which typically requires the execution of drivers. The drivers may or may not be considered part of the engine, but the distinction is not critical.

As used herein, the term database is used broadly to include any known or convenient means for storing data, whether centralized or distributed, relational or otherwise.

Embodiments of the present invention may be provided as a computer program product, which may include a machine-readable storage medium tangibly embodying thereon instructions, which may be used to program a computer (or other electronic devices) to perform a process. The machine-readable medium may include, but is not limited to, fixed (hard) drives, magnetic tape, floppy diskettes, optical disks, compact disc read-only memories (CD-ROMs), and magneto-optical disks, semiconductor memories, such as ROMs, PROMs, random access memories (RAMs), programmable read-only memories (PROMs), erasable PROMs (EPROMs), electrically erasable PROMs (EEPROMs), flash memory, magnetic or optical cards, or other type of media/ machine-readable medium suitable for storing electronic instructions (e.g., computer programming code, such as software or firmware).

Various methods described herein may be practiced by combining one or more machine-readable storage media containing the code according to the present invention with appropriate standard computer hardware to execute the code contained therein. An apparatus for practicing various embodiments of the present invention may involve one or more computers (or one or more processors within a single computer) and storage systems containing or having network access to computer program(s) coded in accordance with various methods described herein, and the method steps of the invention could be accomplished by modules, routines, subroutines, or subparts of a computer program product.

Embodiments of the present invention include various steps, which will be described below. The steps may be performed by hardware components or may be embodied in machine-executable instructions, which may be used to cause a general-purpose or special-purpose processor programmed with the instructions to perform the steps. Alternatively, steps may be performed by a combination of hardware, software, and firmware and/or by human operators.

While some embodiments of the present disclosure have been illustrated and described, those are completely exemplary in nature. The disclosure is not limited to the embodiments as elaborated herein only and it would be apparent to those skilled in the art that numerous modifications besides those already described are possible without departing from the inventive concepts herein. All such modifications, changes, variations, substitutions, and equivalents are completely within the scope of the present disclosure. The inventive subject matter, therefore, is not to be restricted except in the protection scope of the appended claims.

The invention claimed is:

1. A computer-implemented method for non-invasive estimation of a user's pulse rate using only a video camera, the method comprising:

b. capturing, via a monocular RGB video camera operating at $\geq 30$ fps under ambient lighting, a sequence of facial video frames of a subject;

c. detecting candidate skin regions of interest (ROIs) by:

i. segmenting facial landmarks and regions using geometric heuristics or machine learning; and ii. computing a temporal iPPG signal quality metric to select stable pulsatile ROIs;

d. extracting iPPG signals and temporal features from the retained ROIs, including pulse waveform amplitude, harmonics, and temporal SNR;

e. inferring an OCT-variation feature map for each ROI by executing a trained convolutional neural network on the facial video frames, wherein said CNN has been trained to map RGB-video time series to features that emulate structural or coherence-depth patterns characteristic of OCT imaging, without using interferometric OCT hardware during inference;

f. combining the iPPG features and the OCT-variation feature map to generate a fused feature vector;

g. predicting, via a trained model, a pulse rate value from the fused feature vector; and h. outputting, via a display or remote system, the pulse rate together with an interpretability cue identifying the ROI used for inference, Wherein the method is performed by one or more processors executing instructions stored on non-transitory memory, and no physical OCT sensor is used in any step of the method.

2. The method of claim 1, wherein the at least one obtained result indicates the pulse rate level of the user within at least one of a healthy range, a caution range, or an abnormal range category.

3. The method of claim 1, wherein the at least one obtained result is further analyzed to predict one or more potential health conditions of the user based on the at least one obtained result.

4. The method of claim 1, wherein the one or more photoplethysmography imaging (iPPG) variations and the one or more optical coherence tomography (OCT) variations are correlated by the image-based physiological monitoring model to improve accuracy in obtaining the at least one result using the convolutional neural network.

5. The method of claim 1, wherein the at least one image-based physiological monitoring model utilizes an artificial intelligence (AI) technique, a deep learning technique, or a trained machine-learning classifier to obtain the at least one result.

6. The method of claim 1, wherein the at least one image-based physiological monitoring model comprises a convolutional neural network (CNN) algorithm implemented in software to obtain the at least one result.

7. The method of claim 1, wherein processing each frame further comprises applying noise reduction to the frame and performing one or more data augmentations on the noise-reduced frame.

8. The method of claim 1, wherein extracting the one or more facial regions and processing the regions of interest further comprises identifying a plurality of correlated sub-regions within each region of interest for analysis.

9. The method of claim 1, wherein the one or more cameras include an infrared thermal camera, and the method further comprises determining a body temperature of the user based on infrared imaging data captured by the infrared thermal camera.

10. The method of claim 1, wherein the at least one obtained result further comprises an estimation of the blood oxygen saturation ($SpO_2$) level of the user, determined from the real-time video of the user.

11. The method of claim 1, wherein the processor is further configured to display the at least one obtained result on a user interface, the user interface presenting the pulse rate level of the user in at least one of a healthy range, a caution range, or an abnormal range, and further displaying an indication of one or more potential diseases predicted based on the at least one obtained result.

12. A non-contact and non-invasive apparatus for monitoring health characteristics of a user, the apparatus comprising:
    a. one or more sensors configured to non-invasively collect data from the user, including at least one camera sensor for capturing real-time video of the user;
    b. a processor operatively connected to the one or more sensors, the processor configured to:
    c. process the real-time video to extract one or more facial regions in each video frame and identify one or more regions of interest from the facial regions;
    d. apply at least one image-based physiological monitoring model to the one or more regions of interest to determine at least one health-related result for the user, wherein the model uses photoplethysmography imaging data and generates optical coherence tomography (OCT) data via a CNN, without requiring any OCT imaging hardware, to compute the at least one health-related result indicative of the user's pulse rate; and
    e. optionally compare the captured imaging data or the at least one result with standardized physiological information to identify any anomalies in the user's health characteristics;
    f. a communication interface configured to transmit the at least one result to an AI database and to retrieve information from at least one external information source containing standardized physiological data; and
    g. an information analysis system in communication with the processor, the information analysis system being configured to utilize data from the at least one external information source for assisting in the determination of the user's health characteristics.

13. The non-contact and non-invasive apparatus of claim 12, wherein the one or more sensors comprise one or more of: an infrared thermal detector, a temperature sensor, and a camera sensor.

14. The non-contact and non-invasive apparatus of claim 12, wherein:
    a. the data collected by the one or more sensors comprises imaging data associated with the user; and
    b. the imaging data associated with the user is compared with standardized information from the at least one information source to detect one or more of the user's health characteristics, including pulse rate, respiration rate, blood oxygen saturation ($SpO_2$), blood pressure, or body temperature.

15. The non-contact and non-invasive apparatus of claim 12. wherein:
    a. the collected imaging data is fed to an image-based neural network to detect a possible respiratory disease in the user; and
    b. the neural network comprises a machine-learning prediction model selected from the group consisting of: a convolutional neural network (CNN), a support vector machine (SVM), an artificial neural network (ANN), a neuro-fuzzy classifier (NFC), or a neuro-wavelet technique (NWT).

16. The non-contact and non-invasive apparatus of claim 12. wherein the information analysis system includes an artificial intelligence model configured to analyze information from the at least one external information source for one or more gathered physiological parameters of the user.

17. The non-contact and non-invasive apparatus of claim 12. wherein the one or more sensors comprise one or more of: a pulse sensor, a respiration sensor, a temperature sensor, a blood pressure sensor, or a blood oxygen saturation ($SpO_2$) sensor.

\* \* \* \* \*